United States Patent [19]

Mendiratta

[11] 4,447,655
[45] May 8, 1984

[54] PURIFICATION OF BISPHENOL-A

[75] Inventor: Ashok K. Mendiratta, Schenectady, N.Y.

[73] Assignee: General Electric Company, Schenectady, N.Y.

[21] Appl. No.: 444,103

[22] Filed: Nov. 24, 1982

[51] Int. Cl.³ .............................................. C07C 2/58
[52] U.S. Cl. .................................... 568/724; 210/634
[58] Field of Search ............... 210/634, 742, 804, 806; 422/271, 272; 568/724, 750

[56] References Cited

U.S. PATENT DOCUMENTS

| 4,182,921 | 1/1980 | Borgardt et al. | 568/750 |
| 4,192,955 | 3/1980 | Reinitz | 568/724 |
| 4,212,997 | 6/1980 | Adams et al. | 568/724 |
| 4,294,993 | 10/1981 | Li | 568/724 |
| 4,374,283 | 2/1983 | Aneja | 568/724 |

FOREIGN PATENT DOCUMENTS 1149322  4/1969  United Kingdom ............... 568/724

Primary Examiner—Charles N. Hart
Assistant Examiner—Titus B. Ledbetter, Jr.
Attorney, Agent, or Firm—Richard J. Traverso; James C. Davis, Jr.; James Magee, Jr.

[57] ABSTRACT

An efficient method of purifying bisphenol-A is presented whereby solvent washing of the bisphenol-A crystals and extraction of impurities, bisphenol-A and phenol from the aqueous liquid of a water/bisphenol-A crystal slurry is accomplished simultaneously and in a continuous operation. The method involves contacting the water/bisphenol-A crystals with an organic washing solvent in a continuous, multi-stage, countercurrent extraction column.

7 Claims, 1 Drawing Figure

PURIFICATION OF BISPHENOL-A

BACKGROUND OF THE INVENTION

This invention is concerned with the purification of 2,2-bis(4-hydroxyphenyl) propane (hereinafter identified as "bisphenol-A," or "BPA"). More particularly, the invention involves continuous, counter-current treatment of a water/BPA crystal slurry, which is obtained from the aqueous crystallization of crude bisphenol-A, with an organic solvent, thereby simultaneously purifying the bisphenol-A crystals and extracting the bisphenol-A, phenol values and impurities present in the water. One embodiment of this invention can be performed in a continuous, multi-stage, counter-current extraction column.

Bisphenol-A is used in making polycarbonate resins by reaction of the latter with either phosgene or diphenyl carbonate, or for making epoxy resins, both resins being used extensively in commercial applications involving molding, casting, and sheet forming purposes. It is highly important that the monomeric bisphenol-A used to make such resins be as pure as possible in order to avoid adverse effects on the properties of the polymers.

Crude bisphenol-A is the product of commercial processes for preparing bisphenol-A. It is a mixture of bisphenol-A and impurities derived from the BPA synthesis reaction. An example of a reaction which produces crude BPA is the acid-catalyzed condensation of phenol and acetone where phenol and acetone react in the presence of an acidic material such as sulfuric acid, hydrochloric acid, cation exchange resin, etc.

The reaction is usually carried out in excess phenol (>2 moles per mole acetone). The crude bisphenol-A is typically isolated in liquid form from the reaction mixture by a series of distillation steps.

The isolated crude bisphenol-A produced contains undesirable impurities such as the 2-(4-hydroxyphenol)-2-(2-hydroxyphenyl)propane (hereinafter identified as "o,p-isomer") having the formula:

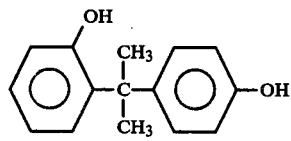

as well as other impurities including phenol itself used in making the bisphenol-A, a trishydroxyphenyl compound of the formula:

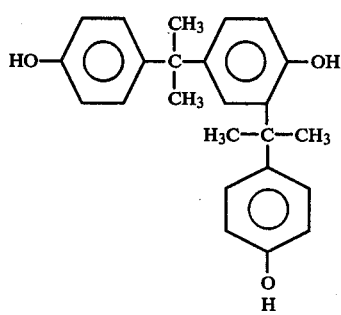

(hereinafter identified as "BPX-1"), small amounts of other impurities such as the two compounds having the formulas:

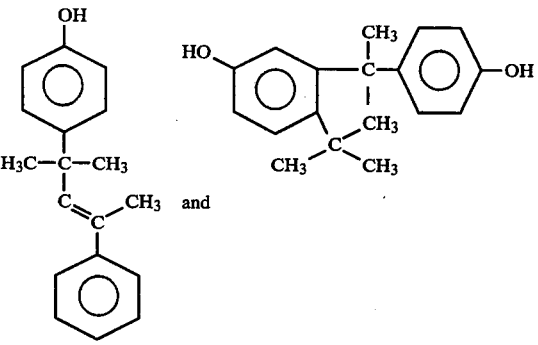

(hereinafter identified as "LD/CD") along with impurities of unknown structure with a yellowish color (herein identified as color bodies), etc.

Typically, the isolated crude bisphenol-A is crystallized in the presence of an organic solvent to free the impurities from the crude bisphenol-A. Crystallization in the presence of an organic solvent produces powdery fine needle-like crystals and permits occlusion by the organic solvent during their formation.

The fine needle-like crystals are difficult to handle, store and dry and, due to the organic solvent occlusion during the crystallization step, the dried product still contains some organic solvent.

A method which uses water as the crystallization medium for bisphenol-A is described in U.S. Pat. No. 3,326,986. According to this patent, the isolated crude bisphenol-A in molten form is mixed with water and the mixture is cooled to yield large, less needle-like crystals of bisphenol-A. Separation of these crystals from the mother liquor, followed by an organic solvent wash results in purification of bisphenol-A. Although the process described within the patent avoids occlusion by an organic solvent during the crystal formation step and yields large, less needle-like crystals, the purification may be limited due to limited washing of the crystals on solid/liquid separation equipment. Theoretically, it should be possible to provide a very effective washing of the crystals obtained from the water crystallization process by repeating the steps of crystal separation, reslurrying the crystals with the organic solvent and then crystal separation. However, such a process scheme is not viable since several complex operating steps and high costs are involved. An effective method of obtaining bisphenol of high purity from an aqueous crystallization process is described and claimed in copending application Ser. No. 443,344 filed Nov. 15, 1982, Mendiratta and Morgan). In this process aqueous crystallized crude bisphenol-A can be treated with an organic solvent while in the presence of water. The organic solvent removes the impurities and the water prevents the adhesion of the organic solvent onto the crystal's surface. The process described in copending application Ser. No. 443,344 filed Nov. 15, 1982 involves a batchwise contact of the water/BPA crystal slurry, produced from the aqueous crystallization step, with an organic solvent. This step is followed by agitation, settling and finally removal of the organic solvent to obtain purified bisphenol-A crystals.

The present invention demonstrates a new and improved process capable of purifying aqueous crystallized bisphenol-A with advantages over the process described in copending application Ser. No. 443,344 filed Nov. 15, 1982 which renders it more suitable for a bisphenol-A manufacturing operation.

One advantage of the present invention is that the extraction of bisphenol-A, phenol and impurities from the aqueous mother liquor and the organic solvent wash of a water/BPA crystal slurry, typically obtained form an aqueous crystallization step, can be accomplished simultaneously and continuously without interruption by intermittent steps, unlike a batchwise operation.

In addition, the present invention can purify bisphenol-A crystals and extract bisphenol-A and phenol from the aqueous mother liquor more efficiently and effectively, requiring less washing solvent than the process described in copending application Ser. No. 443,344 filed Nov. 15, 1982, since it is capable of contacting the water/bisphenol-A crystal slurry with organic solvent counter-currently in multiple stages. Also, the aqueous stream obtained after separation of bisphenol-A crystals can be recycled as such to the aqueous crystallization step, unlike the process disclosed in copending application Ser. No. 443,344 filed Nov. 15, 1982 where it is necessary to extract dissolved phenol, phenolic impurities and bisphenol-A from the recycled aqueous stream. Therefore the water can be recycled to an aqueous crystallization process once separated from the crystals without using additional organic solvent to extract phenol, phenolic impurities, and dissolved bisphenol-A before recycling, as required in the process discussed previously.

SUMMARY OF THE INVENTION

The present invention is based on the discovery that the BPA crystals and aqueous liquid of a water/BPA crystal slurry may be purified simultaneously and continuously through the countercurrent treatment with an organic solvent. This is accomplished by first pumping a water/BPA crystal slurry to form an aqueous crystal stream that has a substantially continuous, downward flow. This aqueous crystal stream is then contacted with an organic solvent stream with a continuous counter current flow at a region of intersecting flow paths. The two streams are mixed at a substantially continuous rate within a portion of the region of contact to wash the impurities from the aqueous liquid and the bisphenol-A crystals passing through the region of contact.

The mixed streams are allowed to settle at the upper and lower periphery of the region of contact at a substantially continuous rate to separate an aqueous crystal phase of purified BPA crystals and aqueous liquid below the region of contact and an organic phase of organic washing solvent and impurities above the region of contact. The purified BPA crystals and aqueous liquid are removed from the isolated aqueous crystal phase as a water/BPA crystal slurry and the organic solvent containing the impurities removed from the water/BPA crystal stream is extracted from the isolated organic solvent phase.

The organic solvent utilized in this process must be immiscible in water and lighter than water and it must be a good solvent medium for impurities expected within the aqueous crystal stream. The operating temperature must be maintained below the melting point of bisphenol-A.

The effectiveness of this process can be increased by continuously mixing the two streams in two or more portions of the region of contact with settling of the mixed streams occuring between each portion to form two intermediate phases of organic solvent and aqueous crystal slurry, respectively.

DESCRIPTION OF THE DRAWINGS

The drawing illustrates in schematic an apparatus suitable for performing the preferred embodiment of the process comprising this invention.

DETAILED DESCRIPTION OF THE INVENTION

Figure 1:
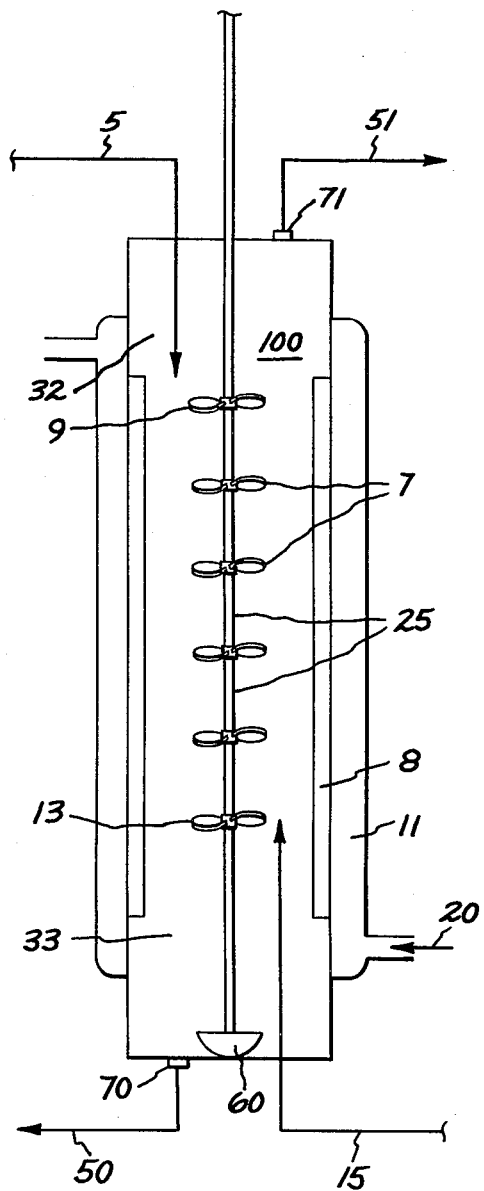

The water/BPA crystal slurries which are typically purified are obtained from a crude bisphenol-A aqueous crystallization process. Not wishing to be restricted to a particular water/BPA crystal slurry or the method of its manufacture, the following example of a method for obtaining a water/BPA crystal slurry is given by way of illustration and does not constitute a part of the invention. Crude bisphenol-A produced from the acid-catalyzed condensation reaction with phenol and acetone is usually recovered from the reaction mixture in liquid form by a series of distillation steps. As a liquid, crystallization in the presence of water can be effected simply by adding water to the liquid crude bisphenol-A, agitating the mixture and allowing the mixture to cool to a temperature in the range of 60° to 70° C. As the mixture cools, crystals form producing a water/BPA crystal slurry suitable for purification process comprising this invention.

The ratio of water to crystals is not critical for the process to function. A sample of a water/BPA crystal slurry with a 2 to 1 ratio of water to crystals was easily purified by this method. The purification process comprising this invention begins by forming an aqueous crystal stream with the water/BPA crystal slurry. This can be accomplished by simply pumping the slurry through a conduit. Any means for forming the aqueous crystal stream is suitable provided the flow is in a substantially downward direction. It is preferable to maintain a continuous flow to permit succeeding steps to be continuously performed and to prevent the equipment utilized from lying idle. Forming this aqueous crystal stream does not physically change the BPA crystals or aqueous liquid within the water/BPA crystal slurry. They are only placed in a state of motion by this procedure.

Once formed, the aqueous crystal stream is subjected to contact with an organic solvent stream in a region where their flow paths intersect. This organic solvent stream can be formed by simply pumping an organic solvent through a conduit. Any means for forming the organic solvent stream is suitable provided the flow is in a direction substantially upward and counter-current to the flow of the aqueous crystal stream. A counter-current flow is preferred since this ensures a substantial portion of the organic solvent stream will intercept and contact a substantial portion of the aqueous crystal stream. The flow of organic solvent can be continuous which ensures that any continuous aqueous crystal stream produced contacts organic solvent.

Contacting the aqueous crystal stream with a stream of organic solvent serves the purpose of washing the surface of the bisphenol-A crystals of impurities, including any phenol, isomeric diphenols, color bodies, etc. The organic solvent also purifies the aqueous liquid of the aqueous crystal stream simultaneously by removing a substantial portion of the impurities, including phenol, isomeric diphenols, bisphenol-A, color bodies, etc. The parameters which define a suitable organic solvent are that the solvent be immiscible in water and lighter than water so that it would form a top surface layer in the presence of water. Another parameter which defines a suitable organic solvent is that the organic solvent provide a good solvent medium for the impurities including phenol, isomeric diphenol, color bodies, etc., found in crude bisphenol-A. Some suitable solvents are, for example, benzene, xylene, toluene, butyl acetate, etc. Toluene is the preferred solvent for washing the bisphenol-A crystals and the aqueous liquid of the aqueous crystal stream.

The amount of organic solvent employed is not critical for bisphenol-A crystal washing or aqueous liquid washing to occur. However, the quantity of organic solvent employed does effect the extent of purification. Bisphenol-A crystals of high purity and an aqueous liquid of high purity have been obtained by employing one half part of organic solvent per part of BPA crystals started with on a weight basis. When trying to conserve organic solvent this quantity is preferred.

To improve the contact between the organic solvent within the region of contact, the two streams are mixed in portions of the region. The mixing can be maintained at a continuous rate to ensure all streams entering the region of contact have been agitated adequately. It is essential that the mixing portions be restricted to the center of the region of contact so that the upper and lower periphery of the region of contact is allowed to settle continuously. An example of how this mixing can be accomplished is to stir the streams with mechanical stirrers within the center of the region of contact. Other means for mixing the two streams are also suitable provided the upper and lower periphery of the region of contact is allowed to settle.

The efficiency and effectiveness of this invention can be increased if the two stream are mixed in multiple isolated portions with settling of the two streams occurring between each portion. To obtain improved results, the settling between each isolated mixing portion must be sufficient enough to form two small intermediate phases, each pair including an intermediate aqueous crystal phase and an intermediate organic solvent phase. Each isolated mixing portion provides a separate washing of the aqueous crystal stream that passes through it. The more isolated mixing portions utilized, the more the aqueous crystal phase is washed.

The use of one mixing portion will permit purification of the bisphenol-A and aqueous liquid of the aqueous crystal stream to occur. However, the degree of purification is dependent on the number of these mixing portions along with the size of these mixing portions and degree of agitation within each portion. In the preferred embodiment bisphenol-A of high purity, along with a highly pure aqueous liquid, has been obtained utilizing six isolated mixing portions in a multiple stage counter-current extraction column shown in FIG. 1 and further described in Example III. This process and its preferred embodiment are not limited to such an apparatus to function or to obtain bisphenol-A and an aqueous liquid of high purity. Alternative means for mixing the two streams within the center of the region of contact are suitable for this process provided the upper and lower periphery of the region of contact is allowed to settle.

The mixture of the two streams must be allowed to settle at the lower periphery of the region of contact so as to isolate a lower aqueous crystal phase. This phase comprises purified BPA crystals and a purified aqueous liquid which have passed through the region of contact as part of the aqueous crystal stream. This aqueous crystal phase forms due to a higher density than the organic solvent which causes it to fall below the organic solvent when settled.

The mixture of the two streams must also be allowed to settle at the upper periphery of the region of contact so as to isolate an upper organic solvent phase. This phase is essentially the organic solvent stream with impurities removed from the aqueous crystal stream including, for example, phenol, diphenols, color bodies, dissolved BPA, etc. This organic solvent phase is formed above the region of contact due to the fact that the organic solent has a lower density than the aqueous crystal stream which causes it to rise above the aqueous crystal stream when settled.

The settling which takes place at an upper and lower periphery of the region of contact can be performed at a continuous rate in this process which permits succeeding and preceeding steps to operate continuously.

The purified bisphenol-A crystals and the purified aqueous liquid are recovered together from the aqueous crystal phase in the form of a solid-liquid slurry. The crystals and liquid can be removed at a continuous rate by this process. This is particularly important when all the preceeding steps are operating continuously.

The organic solvent containing substantially all the impurities within the bisphenol-A crystals and aqueous liquid which it contacted can be extracted from the organic solvent phase at a substantially continuous rate also. As with the recovery of purified crystals and aqueous liquid from the aqueous crystal phase, extracting the solvent at a continuous rate is particularly important when all the preceeding steps are operating continuously.

The process comprising this invention must be performed at a temperature below the melting point of bisphenol-A so that the BPA crystals do not melt and dissolve in the organic solvent. This would diminish the quantity of purified BPA recovered and reduce the effectiveness of the purification process comprising this invention. The temperature maintained during the operation of the process steps is preferably at a value within the range of 40°–85° C.

Once the purified BPA crystals and purified aqueous liquid are recovered as a solid liquid slurry, the BPA crystals can be separated from the slurry with conventional solid-liquid separation equipment such as a basket centrifuge. The aqueous liquid left remaining is suitable for use in a crude bisphenol-A aqueous crystallization process since substantially all the impurities within it, including phenol, have been removed. The simultaneous purification of the aqueous liquid eliminates the need for a separate purification process to remove impurities, including phenol, phenolic derivatives, etc., from the aqueous liquid before recycling it back to an aqueous crystallization process. This conserves the costly organic solvents which are necessary to remove impurities from the aqueous liquid.

Samples of bisphenol-A crystals produced from this process approach 100% purity with no impurities being detected by liquid chromatograph analysis, melting point tests, and absorbance values. The quality of the purified bisphenol-A crystals obtained from this process is very high since the crystals were not formed in the presence of an organic solvent which permits occlusion. In addition, the crystals are washed more efficiently due to the presence of water in the washing step. The product is only water-wetted which need not be completely dried if used to form polycarbonate.

This invention provides major advantages over the process described in U.S. Pat. No. 3,326,986 in that the washing of the surface impurities from the aqueous crystallized bisphenol-A is simpler and more efficient, producing a purer bisphenol-A product. In addition, this produce is only water-wetted which need not be completely dried if used to form polycarbonate.

The invention also provides major advantages over the batchwise operation described in copending application Ser. No. 443,344 filed Nov. 15, 1982 in that this invention permits all steps to be operated continuously which improves the efficiency of the process since the equipment utilized need not lie idle. The equipment utilized is also much simpler since the coordination of the termination and initiation of different steps is not necessary. This process also produces a better bisphenol-A crystal product utilizing less organic washing solvent due to the multiple stage treatments. Finally this process also saves organic solvent in that the aqueous liquid is purified sufficiently to be recycled in an aqueous crystallization process.

In order that those skilled in the art may better understand the present invention and how it may be practiced, the following examples are given by way of illustration and not by way of limitation.

EXAMPLE I

A control sample of purified BPA crystals was obtained by first mixing molten crude bisphenol-A having 4% impurities, (including phenol) and an I.A. value of 2.00 (initial absorbance value (I.A.) is the relative color content value which was measured as the absorbance of a 10 solution, 5 gms diluted with 50 mls methanol, in a 10 cm cell at 350 mn wavelength) with 2 parts water. The mixture was cooled gradually to obtain BPA crystals in a water/BPA crystal slurry. This slurry was maintained at 65° C. and centrifuged in a basket centrifuge to separate the solid crystals. The crystals were then washed with 2 parts of toluene on the centrifuge. The resulting BPA crystals had an absorbance value of 0.25 and 0.2% impurities.

EXAMPLE II

Another sample of purified BPA crystals was obtained by the batch-wise process described in copending application Ser. No. 443,344 filed Nov. 15, 1982 utilizing less organic washing solvent than is preferred for that process. Molten crude bisphenol-A (I.A. 2.00, impurities 4% by weight including phenol) was mixed with 2 parts of water. The mixture was cooled gradually to crystallize bisphenol-A and form a water/BPA crystal slurry when the temperature in the crystallizer reached 65° C., ½ part of toluene per part of crude bisphenol-A on a weight basis was added to the mixture. After agitating the bisphenol-A crystals/water/toluene mixture for 10 minutes, the mixture was allowed to settle. Three phases were observed. The top phase was decanted and the bisphenol-A crystals were recovered from the remaining water/bisphenol-A crystal slurry with the help of a basket centrifuge. The recovered bisphenol-A crystals had an I.A. value of 0.15 and negligable detectable impurities. The mother liquor aqueous liquid had 0.5 weight percent phenol and trace quantities of calibrated impurites associated with bisphenol-A.

EXAMPLE III

A sample of BPA crystals and aqueous liquid was produced according to the process comprising this invention by first producing a large batch of a water/bisphenol-A crystal slurry by mixing molten crude BPA having 4% impurities (including phenol) and a 2.00 absorbance value with 2 parts of water. The mixture was cooled gradually to 65° C. to yield BPA crystals. The BPA crystal/water slurry was maintained at a temperature of 65° C.

The slurry was then fed into a multistage counter-current extraction column where the process comprising this invention was performed. FIG. 1 shows a multistage counter-current extraction column 100 of 3 inches in diameter and 30 inches high. It is equipped with six pitched blade turbine impellers 7 positioned in the center and vertical baffles 8 on the side walls so as to restrict mixing to six isolated portions and allow settling in portions 25 between the impellers. The column is also designed to permit isolation of an aqueous crystal phase in a region 33 located below the impellers and isolation of an organic phase in a region 32 located above the impellers. The column also utilized a small impeller 60 in the isolated aqueous crystal stream to prevent BPA crystals within the aqueous crystal phase. Hot oil, shown by line 20, is circulated through the column jacket 11 to maintain the temperature at 65° C.

The process comprising this invention was begun by continuously pumping a water/BPA crystal slurry as described above, shown as line 5, to the top turbine impeller 9 of the multi-stage counter-current extraction column 100, which defines the upper periphery of the region of contact. The stream produced was contacted with a toluene stream, shown as line 15, feeding toluene to the bottom turbine impeller 13 of the multi-stage counter extraction current column which defines the lower periphery of the region of contact. One half part of toluene was used for every part of crude BPA in the slurry. The two streams were then mixed by the six turbine impellers 7. The contents of the lower aqueous crystal phase shown as line 50 and the contents of the upper organic phase shown as line 51 were recovered from the multi-stage counter-current extraction column through outlets 70 and 71 respectively. All the processes described above were performed continuously. The BPA crystals were separated from the solid/liquid slurry recovered from the aqueous crystal phase in a basket centrifuge. The BPA crystals had an absorbance value of 0.11 with no detectable impurities. The aqueous liquid remaining after the crystals were separated contained 0.2 weight percent phenol and no detectable impurities.

While the invention has been described in detail and with reference to specific embodiments thereof, it will be apparent to one skilled in the art that various changes and modifications can be made therein without departing from the spirit and scope of the invention.

What I claim as new and desire to secure by Letters Patent of the United States is:

1. A process for simultaneously and continuously purifying the bisphenol-A crystals and the aqueous liquid of a water/BPA crystals slurry, said process comprising the steps of:
   (a) forming an aqueous-crystal stream from a water/BPA crystals slurry, said aqueous-crystal stream having a flow which is substantially downward and continuous;

(b) contacting said aqueous-crystal stream with a stream comprising an organic solvent in a region of intersecting paths, the stream of organic solvent having a flow in a direction substantially upward and counter-current to the flow of said aqueous crystal stream, said organic solvent being immiscible in water, lighter than water and a good solvent medium for impurities within said aqueous liquid and bisphenol-A crystals;

(c) mixing the aqueous-crystal stream and the organic solvent stream passing through the region of contact in the center of said region of contact;

(d) forming a lower aqueous-crystal phase below the the region of contact and an upper organic solvent phase above the region of contact;

(e) recovering purified bisphenol-A crystals and purified aqueous liquid from said lower aqueous-crystal phase;

(f) removing organic solvent with extracted impurities from said upper organic solvent phase;

said process being performed at a temperature below the melting point of said bisphenol-A crystals.

2. A process for simultaneously and continuously purifying the bisphenol-A crystals and the aqueous liquid of a water/BPA crystals slurry, said process comprising the steps of:

(a) forming an aqueous-crystal stream from a water/BPA crystals slurry, said aqueous-crystal stream having a flow which is substantially downward and continuous;

(b) contacting said aqueous-crystal stream with a stream comprising an organic solvent in a region of intersecting flow paths, the stream of organic solvent having a flow in a direction substantially upward and counter-current to the flow of said aqueous-crystal stream, said organic solvent being immiscible in water, lighter than water and a good solvent medium for impurities within said aqueous liquid and bisphenol-A crystals;

(c) mixing the aqueous-crystal stream and the organic solvent stream passing through the region of contact in multiple isolated portions of said region of contact;

(d) forming two small intermediate phases between each isolated mixing portion, the intermediate phase pairs comprising an aqueous crystal phase and an organic solvent phase;

(e) forming a lower aqueous-crystal phase below said region of contact and an upper organic phase above said region of contact;

(f) recovering purified bisphenol-A crystals and purified aqueous liquid from said lower aqueous crystal phase, and (g) removing organic solvent with extracted impurities from said upper organic solvent phase, said process being performed at a temperature below the melting point of said bisphenol-A crystals.

3. A process in accordance with claim 2 wherein the organic solvent utilized to form said organic solvent stream is toluene.

4. A process in accordance with claim 2 wherein the temperature at which said process is performed is selected from a value within the range of 40° C. to 85° C.

5. A process in accordance with claim 2 wherein one half part of organic solvent is utilized to form said organic solvent stream for every part of the bisphenol-A crystals within said water/BPA crystal slurry to be purified on a weight basis.

6. A process in accordance with claim 2 further comprising the step of separating said purified bisphenol-A crystals from said lower aqueous-crystal phase.

7. A process in accordance with claim 6 further comprising the step of crystallizing crude bisphenol-A in the purified aqueous liquid of said lower aqueous-crystal phase.

* * * * *